United States Patent
Meloff et al.

(10) Patent No.: US 9,662,094 B2
(45) Date of Patent: May 30, 2017

(54) LIQUID SAMPLE COLLECTING SYSTEM

(71) Applicants: Colleen Meloff, Tampa, FL (US); Brett J. Epstein, Jupiter, FL (US)

(72) Inventors: Colleen Meloff, Tampa, FL (US); Brett J. Epstein, Jupiter, FL (US)

(73) Assignee: Colleen Meloff, Tampa, FL (US)

( * ) Notice: Subject to any disclaimer, the term of this patent is extended or adjusted under 35 U.S.C. 154(b) by 50 days.

(21) Appl. No.: 14/688,294

(22) Filed: Apr. 16, 2015

(65) Prior Publication Data

US 2015/0297194 A1 Oct. 22, 2015

Related U.S. Application Data

(60) Provisional application No. 61/980,098, filed on Apr. 16, 2014.

(51) Int. Cl.
*A61B 5/00* (2006.01)
*A61B 10/00* (2006.01)
*A01K 23/00* (2006.01)

(52) U.S. Cl.
CPC ........ *A61B 10/007* (2013.01); *A61B 10/0038* (2013.01); *A01K 23/005* (2013.01)

(58) Field of Classification Search
CPC .............. A61B 10/0045; A61B 10/007; A61B 10/0038; A01K 23/005
See application file for complete search history.

(56) References Cited

U.S. PATENT DOCUMENTS

| | | | | |
|---|---|---|---|---|
| 5,492,220 A | * | 2/1996 | Estay | A61B 90/50 206/363 |
| D456,898 S | * | 5/2002 | Yang | D24/122 |
| 6,719,951 B1 | * | 4/2004 | Griffith | A61B 10/007 215/396 |
| 6,973,678 B2 | * | 12/2005 | Jones | A61B 10/0096 4/144.1 |
| 7,128,352 B1 | * | 10/2006 | Phippen | A01K 23/005 119/161 |
| 8,091,848 B1 | * | 1/2012 | Reed | A61B 10/007 220/737 |
| 8,465,440 B1 | * | 6/2013 | Grayson | A61B 10/007 600/573 |
| D706,947 S | * | 6/2014 | Hooper | D24/227 |

* cited by examiner

*Primary Examiner* — Max Hindenburg
(74) *Attorney, Agent, or Firm* — The Weintraub Group, P.L.C.

(57) ABSTRACT

In accordance with the present invention, there is provided a liquid sample collection system, which generally comprises a means for grasping or a handle 12(*b*) a collection container or cup. The handle is an intervally formed unitary member having a first end or section, a medial section, angularly inclined with respect to the first section and a third section extending from the second section and substantially parallel to the first section.

4 Claims, 2 Drawing Sheets

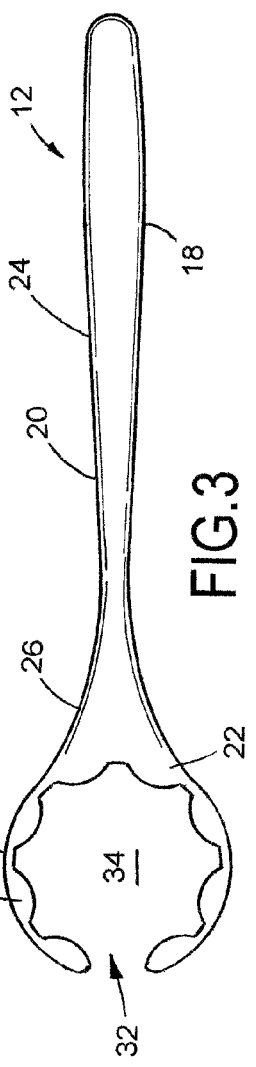
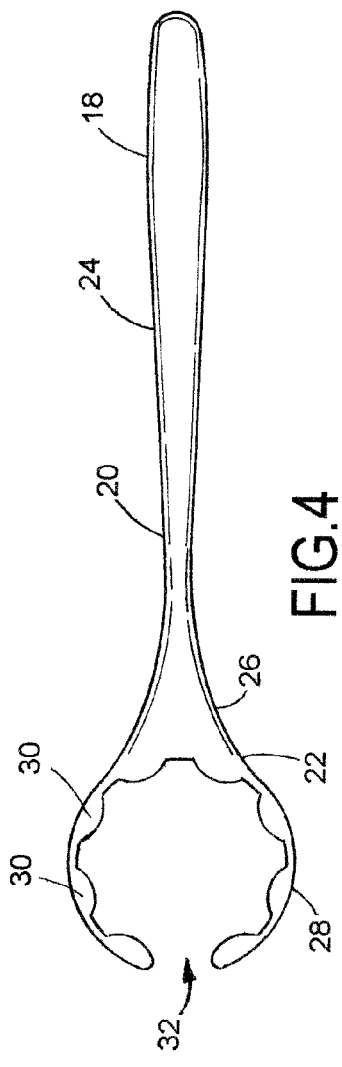
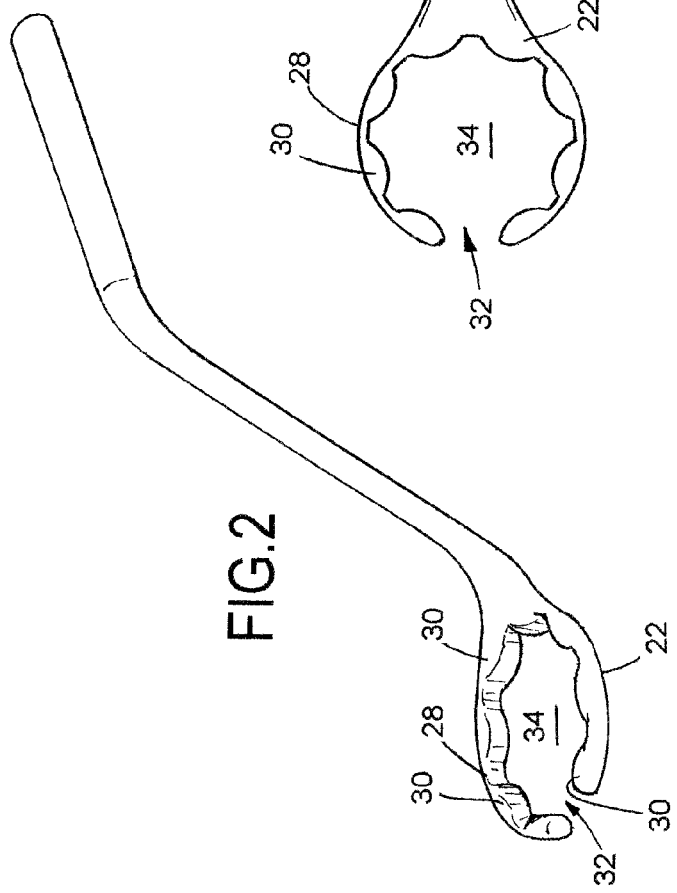
FIG.2
FIG.3
FIG.4

LIQUID SAMPLE COLLECTING SYSTEM

CROSS-REFERENCED RELATED APPLICATIONS

This application is a completion application of U.S. Provisional Patent Application, Ser. No. 61/980,098, filed Apr. 16, 2014 for "Liquid Sample Collecting System," the entire disclosure of which is hereby incorporated by reference, including the drawing.

BACKGROUND OF THE INVENTION

1. Field of the Invention

The present invention concerns liquid sample collecting systems. More particularly, the present invention concerns collection of biologic fluids. Even more particularly, the present invention pertains to devices for facilitating collection of biologic fluids by third parties.

2. Prior Art

The collection of biologic fluids, such as urine samples, from non-ambulatory men and women as well as from women, themselves generally, involves having the person seated on a toilet and then an aide or third-party struggles to collect the sample. Even if the person himself or herself attempts to collect the sample, this is often a difficult and messy task.

The prior art has struggled with this dilemma but has never been able to arrive at a satisfactory solution.

In U.S. Pat. No. D654,598, there is disclosed a handle and cup assembly which attempts to solve this problem. However, because of the configuration of the handle, the efficacy of the device is constrained. Typically, when a person is seated on a toilet, that person's genital area is downwardly directed into the toilet bowl. Therefore, any collection attempted with this prior device is cumbersome, awkward and can, in many instances, lead to discomfiture because of the perpendicularity of each handle segment to each other.

As detailed hereinafter the present invention improves upon such prior collection system which facilitates the collection without encountering the prior problems.

SUMMARY OF THE INVENTION

In accordance with the present invention, there is provided a liquid sample collection system, which generally comprises: (a) means for grasping or a handle and (b) a collection container or cup.

The handle is an integrally formed unitary member having a first end or section, a second or medial section, angularly inclined with respect to the first section and a third section extending from the second section and substantially parallel to the first section.

The third section comprises a substantially circular c-shaped seating portion for removably seating a collection cup.

Optionally, a plurality of radiating fingers or nubs can protrude inwardly of the circular seating portion to facilitate retention of the collection cup within the third section.

The present collection system facilitates the collection of bodily fluids and/or other discharges for sampling within the cup for subsequent diagnostic evaluation or to promote more sanitary conditions for non-ambulatory persons.

Because of the length of the handle, the administrator or user, such as a nurse, aid, care giver, or the like never touches either the discharge or the person or patient, rendering a sanitary collection system.

For a more complete understanding of the present invention, reference is made to the following detailed description and accompanying drawing. In the drawing, like reference characters refer to like parts throughout the several views in which:

BRIEF DESCRIPTION OF THE DRAWING

FIG. 2 is a perspective view of the handle used in the practice of the present invention;

FIG. 3 is a top view of the handle used in the present system, and

FIG. 4 is a bottom view thereof.

DESCRIPTION OF THE INVENTION

Figure 1:
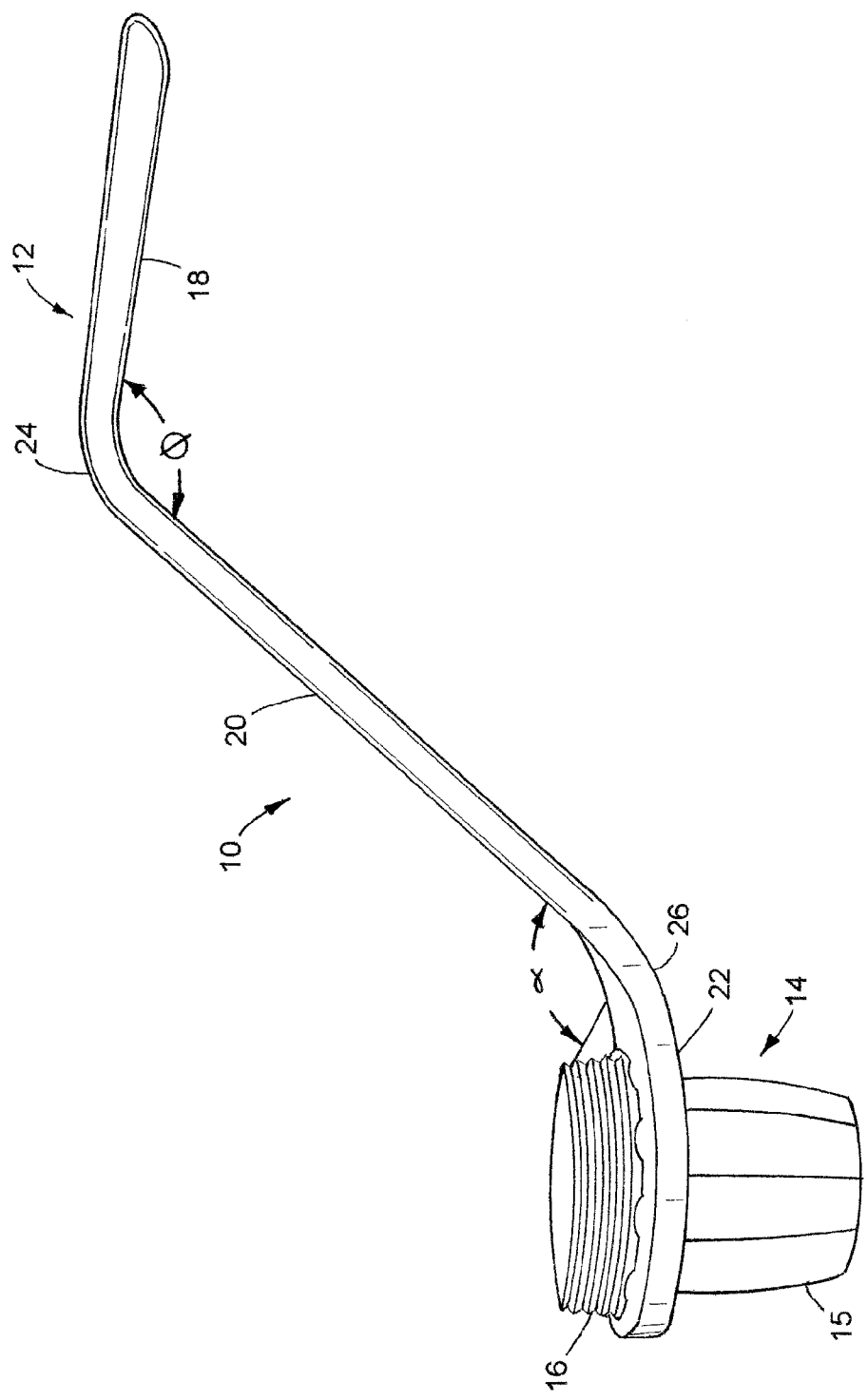
FIG. 1 is a side elevational view showing the present collection system.

Now, and with reference to the drawing, there is depicted therein a liquid sample collection system for collecting biologic fluids, generally, denoted at 10. The system 10, generally, comprises (a) means for grasping or handle 12 and (b) a collection container or collection cup 14.

The collection cup 14 is a standard collection cup which is well known and commercially available. Such cups are ordinarily found in medical supply houses as well as doctors' offices and the like. These collection cups, generally, comprise an open top collector 15 having a threaded neck, as at 16, in which, once a sample is collected, a cap (not shown) is threadably connected to the collector 15.

The handle or means for grasping 12 comprises a first or grasping section 18, a second or medial section 20, and a third or collector enveloping section 22.

The first section 18 is an elongated element suitably dimensioned to enable either a third-party or the user himself or herself to grasp the first section 18 either with an entire hand or with any requisite number of digits to provide a stable holding of the collection cup 14, as detailed below.

The medial section 20 is angularly disposed with respect to the first section 18 by an angle Ø. The medial section 20 is integrally formed with the first section 18 at a first end 24 thereof. The angle Ø, generally, ranges from about 25 to 65 degrees and, preferably, from about 35 to about 60 degrees.

The opposite end 26 of the medial section 20 merges with and is integrally formed with the collection cup enveloping or retaining third section 22. The third section 22 is angularly disposed with respect to the medial section by an angle ɑ. The angle ɑ ranges from about 115 degrees to about 155 degrees in opposition to the angle Ø.

As shown, the first section 18 and the third section 22 are substantially parallel to each other with the medial section 20 angularly disposed therebetween at an angle substantially less than 90 degrees.

As shown in FIGS. 2-4, the third section 22, which is integrally formed with the medial section 20, comprises a substantially C-shaped wall 28 having an opening 32 and which defines an open interior 34.

A plurality of circumferentially disposed spaced apart nubs or fingers 30 project into the interior 34. The nubs 30 are formed on the interior surface or face of the wall 28, as shown.

Although the nubs 30 are shown as semi-circular any other optimal configuration can be used. However, the semi-circular geometry is preferred because of the ease of manufacture.

The nubs 30 are integrally formed with the C-shaped wall 28.

The means for grasping 12 is preferably formed from a substantially rigid plastic material such as HDPE, polyethylene, ABS, or the like. However, the opposed ends of the opening 32 and the manufacture of the third section 22 either has sufficient flexibility to enable the third section 22 to encircle, contact or hold the collection cup 14 about its neck 16, as shown. Alternatively, the collection cup 14 can be inserted into the open interior 34 by inserting it bottom first into the open interior 34 and pushing downwardly.

The angulation and the length provided to the means for grasping 12 and, in particular, the medial section 20, enables a third-party or the user himself or herself to place the collection cup 14 proximate the genital area from which the biologic fluid or urine sample is to be collected with greater facility and at a greater distance than that shown in the prior art.

This is especially true when the system 10 is used by a third-party who, without any awkwardness, can place the collection cup 14 proximate the genital area, be it vaginal or penile, to facilitate the collection of a urine sample.

Again, because of the angular relationship, there is no spillage after the sample is collected. Furthermore, because the third-party maintains a distance, not only from the collection cup 14 but from the person or user, the system 10 maintains a sanitary condition.

It is to be appreciated from the preceding that there has been described herein a system for collecting bodily discharges, especially urine and fecal matter in a convenient and sanitary manner.

The invention claimed is:

1. A system for collecting a bodily discharge from the body of a person, comprising:
   (a) a collection cup;
   (b) means for grasping including a first section, a medial section, and a third section, the third section defined by a substantially C-shaped circular wall having an open interior to removably seat the collection cup, the first and third sections being substantially parallel to each other with the medial section angularly disposed with respect to the first and third sections, the first section being disposed at an angle of from about 25 degrees to about 65 degrees with respect to the medial section, the third section being disposed at an angle of from about 115 degrees to about 155 degrees with respect to the medial section, and
   wherein the angulation of the first section and the third section with respect to the medial section cooperate with the length of the medial section to provide a sufficient distance between the first and third sections to maintain a sanitary environment between a user and the collection cup.

2. The device of claim 1 which further comprises: a plurality of nubs formed on an interior surface of the circular wall and projecting radially inwardly toward the center thereof.

3. The device of claim 1 wherein the circular wall has an outer surface and an interior surface, a plurality of nubs circumferentially disposed about the interior surface and projecting inwardly toward the center of the circular wall.

4. The device of claim 3 wherein the collection cup is removably seated in the open center of the circular wall, the top of the collection cup engaging the top of the circular wall and being emplaced therein in a stable condition by the plurality of nubs.

* * * * *